United States Patent [19]

Modrovich

[11] Patent Number: 5,112,769

[45] Date of Patent: May 12, 1992

[54] STABLE SINGLE LIQUID REAGENT FOR DETERMINATION OF DIRECT BILIRUBIN IN SERA AND METHOD OF FORMING SAME

[76] Inventor: Ivan E. Modrovich, 96 Natalie Way, Camarillo, Calif. 93010

[21] Appl. No.: 602,006

[22] Filed: Oct. 19, 1990

Related U.S. Application Data

[63] Continuation-in-part of Ser. No. 357,023, May 25, 1989, Pat. No. 4,965,210, which is a continuation-in-part of Ser. No. 101,776, Sep. 29, 1987, abandoned.

[51] Int. Cl.$^5$ ............................................. G01N 33/72
[52] U.S. Cl. ...................... 436/97; 436/166; 436/903
[58] Field of Search ......................... 436/97, 166, 903

[56] References Cited

U.S. PATENT DOCUMENTS

| | | | |
|---|---|---|---|
| 3,585,004 | 6/1971 | Mast | 436/97 X |
| 4,038,031 | 7/1977 | Lam | 436/903 X |
| 4,119,401 | 10/1978 | Sansur et al. | 436/97 |
| 4,311,483 | 1/1982 | Perry | 436/97 X |
| 4,965,210 | 10/1990 | Modrovich | 436/166 X |

FOREIGN PATENT DOCUMENTS 0140642  8/1983  Japan ..................................... 436/97

*Primary Examiner*—Robert J. Hill, Jr.
*Attorney, Agent, or Firm*—Christie, Parker & Hale

[57] ABSTRACT

There is provided a stable liquid single reagent solution for determination of conjugated bilirubin in biological fluids which comprises an essentially surfactant free aqueous solution containing a positive amount of a water soluble organic sulfate, a diazonium salt, urea and a heavy metal complexing agent, the solution having an acidic pH and stable for at least 18 months at 2° to 8° C. Also disclosed is a method of forming such a reagent.

17 Claims, No Drawings

STABLE SINGLE LIQUID REAGENT FOR DETERMINATION OF DIRECT BILIRUBIN IN SERA AND METHOD OF FORMING SAME

CROSS REFERENCE TO RELATED APPLICATIONS

This application is a continuation-in-part of U.S. application Ser. No. 07/357,023, filed May 25, 1989, now U.S. Pat. No. 4,915,210, incorporated herein by reference, which is a continuation-in-part of application Ser. No. 07/101,776, filed Sept. 29, 1987, now abandoned, also incorporated herein by reference.

BACKGROUND OF THE INVENTION

Bilirubin is a reddish yellow substance found in biological substances, such as blood serum, and has the empirical formula: $C_{33}H_{36}N_4O_6$.

Bilirubin is an end product of hemoglobin catabolism. It is conjugated with glucuronic acid in the liver, and the conjugated form is cleared from the circulation by excretion into bile. Both conjugated (direct) and unconjugated (indirect) forms of bilirubin (total bilirubin) circulate loosely bound to albumin. Conjugated bilirubin, as the glucuronide, is a mono and/or diester, reported the structures and chromogen forming reactions of which are reported in "Bilirubin Volume I" Heirwegh et al, CRC Press, 1982 at page 1237 incorporated herein by reference and is measured by direct bilirubin methods.

Elevated serum bilirubin levels are observed in a variety of conditions, including hemolytic disorders, biliary obstruction, cholestasis, hepatitis, cirrhosis, and decreased conjugation (e.g., neonatal jaundice). In obstructive jaundice, there is an increase in the total bilirubin that is primarily due to the glucuronide fraction. In hemolytic jaundice and in neonatal jaundice, the increase is primarily due to the unconjugated bilirubin fraction. In the newborn, jaundice may be caused by Rh, ABO, or other blood group incompatibilities, by hepatic immaturity, or by hereditary defects in bilirubin conjugation. Both conjugated and unconjugated bilirubin are increased in cirrhosis and hepatitis. The relative proportion of the conjugated fraction increases with progression of the disease until eventually the liver loses its ability to carry out the conjugation process.

It is apparent that while an assay for total bilirubin is important to obtain a total assessment of human condition determination of direct or conjugated bilirubin is also of significant importance.

Most bilirubin assays are based upon variations of the classical method of Van Den Bergh and Mueller in which diazotized sulfanilic acid and bilirubin, in an acidic solution, react to form azobilirubin. Accelerators and solubilizers are added to total bilirubin procedures to ensure complete reaction of unconjugated bilirubin.

The present invention is directed to a stable liquid assay composition for the quantitative determination of serum direct or conjugated bilirubin in the diagnosis and treatment of liver, hemolytic hematological, and metabolic disorders, including hepatitis and gall bladder block.

SUMMARY OF THE INVENTION

The present invention provides a single reagent system of an excellent shelf stability of at least 18 months at 2 to 8.C, and is highly responsive to the quantitative measurement of conjugated bilirubin in biological fluids, such as blood serum at 520 to 575 nanometers (nm).

A stable liquid single reagent solution for determination of direct bilirubin in sera comprises an essentially surfactant free aqueous solution containing a diazonium salt in an amount sufficient to diazonize the direct bilirubin to a detectable chromogen, the intensity of which is function of direct bilirubin concentration, a water soluble organic sulfate present in amount sufficient to catalyze the diazo reaction and the complex absorbance more intense, and stabilize the diazonium salt against degradation; urea in amount sufficient to solubilize protein and a heavy metal complexing agent present in amount sufficient to complex with heavy metal ions. The solution is a sufficiently acidic pH so as to hinder solubility of unconjugated bilirubin.

Preferably the composition comprises an essentially surfactant-free aqueous solution of: a positive amount up to about 10 preferably about 2 to about 7.5 grams per liter (g/l) of a water soluble organic sulfate which may be a long chain aliphatic sulfate, an aromatic sulfate or mixtures thereof, preferably 5-sulfosalicylic acid, p-toluenesulfonic acid, or mixtures thereof; from about 0.01 to about 0.03 g/l of a diazonium salt, preferably 3,5-dichlorophenyl diazonium tetrafluoroborate at a concentration of about 0.02 g/l; from about 20 to about 30 g/l, preferably about 26 g/l, urea; and a heavy metal complexing agent, preferably ethylenediaminetetracetic acid (EDTA) present in an amount sufficient to complex with heavy metal ions. Normally, EDTA concentration is about 0.05 g/l. The solution is highly acidic with a pH less than 1, and preferably induced by sulfuric and/or hydrochloric acids.

To achieve long term stability and functionality, the composition is prepared by first adding the complexing agent (EDTA) to water, followed by dissolving the organic sulfate, then acidifying the solution, preferably first with sulfuric then hydrochloric acid, followed by urea then finally dissolving the diazonium salt.

The resulting mixture is stable for at least 18 months at 2 to 8° C. which is a time sufficient to enable manufacture, worldwide shipment, warehousing and storage until use. The composition is kept in a dark amber container to ensure light stability.

DETAILED DESCRIPTION

There is provided in accordance with the present invention a single reagent composition of excellent shelf life and rapid response which enables the quantitative assay of direct bilirubin concentration in human serum.

The composition is an aqueous solution of at least one diazonium salt, preferably 3,5-dichlorophenyl diazonium tetrafluoroborate present in a concentration of from about 0.01 to about 0.03 g/l, preferably about 0.02 g/l; a positive amount of up to about 10 g/l of an organic sulfate where the organic moiety is a long chain aliphatic group, an aromatic group and mixtures thereof. The preferred organic sulfate is 5-sulfosalicylic acid at a concentration of about 2 g/l. Paratoluene sulfonic acid at a concentration of about 7.5 g/l can also be effectively used. There is also present from about 20 to about 30 g/l, preferably about 26 g/l urea, and ethylene-diaminetetracetic acid (EDTA) in sodium salt form present in a concentration sufficient to complex with any heavy metal ions which are present. The current preferred concentration of EDTA is about 0.05 g/l.

The solution, essentially surfactant-free, normally has a pH less than 1, preferably by addition of sulfuric and/or hydrochloric acids.

The composition is critically prepared by first adding EDTA to distilled water to complex any heavy metals which are present; the water soluble organic sulfates are added and dissolved. This is followed by acidulation with sulfuric and hydrochloric acids. This is followed by addition and dissolution of urea. The diazonium salt is added last. The solution as prepared is stable at temperatures of abut 2.C to about 8.C (refrigeration conditions) for at least 18 months.

In the system, the diazonium salt diazotizes the bilirubin forming a chromogen which is red in color. The water soluble organic sulfate acts to catalyze the diazo reaction, make the complex absorbance more intense, and stabilize the diazonium salt ,against degradation. Urea enhances protein solubility and this is is critical to prevent the reaction mixture from becoming turbid and influencing the measurement of reaction product with a spectrophotometer. The mineral acids reduce interference from free bilirubin, the absence of a surfactant insures specificity for bilirubin in its conjugated form.

The assay system of this invention is suited to the measurement of the conjugated fraction of total bilirubin at a completion time of less than two minutes for the composition shown in Table 1. The actual completion time for the reaction is less than one minute.

TABLE 1

| Components | Direct Bilirubin (per liter) |
|---|---|
| EDTA-$Na_2$ | 0.05 g |
| 5-Sulfosalicylic Acid | 2.0 g |
| 50% $H_2SO_4$ | 80 ml |
| Conc. HCl | 14 ml |
| Urea | 25.0 g |
| 3,5-dichlorophenyl diazonium tetrafluoroborate | 0.02 g |
| pH | <1.0 |

For purposes of an analysis the direct bilirubin reagent is supplied ready to use with a bilirubin blank, ready to use. The bilirubin blank is of the same composition as the direct bilirubin reagent but does not contain the diazonium salt. In the procedure, to 1.0 mililiter bilirubin reagent then is added 50 microliters sample; both are immediately mixed and incubated for 2 minutes at an assay temperature of 25, 30 or 37° C. To 1.0 mililiter of a bilirubin blank there is also added 50 microliters of the sample. Again, both are immediately mixed and incubated for 2 minutes at assay temperature. The spectrophotometer is zeroed at 560 nm using a reagent blank (1.0 mililiters bilirubin reagent +50 microliters distilled water). The absorbance of each tube is measured and the absorbance of the bilirubin blank sample is substracted from the absorbance obtained for the corresponding test sample.

A liquid direct bilirubin standard is used to calibrate the spectrophotometer with ratio of the concentration of standard to its absorbance is used to supply a multiplier which when multiplied by the difference between sample and blank absorbance gives concentration of direct bilirubin in the sera. The chemTrak TM brand of direct bilirubin standard manufactured by Medical Analysis Systems may be used for this purpose.

What is claimed is:

1. A stable liquid single reagent solution for determination of direct bilirubin in sera which comprises an essentially surfactant free aqueous solution containing a diazonium salt in a concentration sufficient to diazonize conjugated bilirubin to a detectable chromogen, an organic sulfate present in a concentration sufficient to at least stabilize the diazonium salt, urea in an amount to solubilize protein, a heavy metal complexing agent present in amount sufficient to complex with heavy metal ions, said solution having an acidic pH less than 1 and sufficiently low to hinder solubilization of unconjugated bilirubin said reagent being stable for at least 18 months at 2 to 8°πC.

2. A solution as claimed in claim 1 in which the diazonium salt is 3,5-dichlorophenyl diazonium tetrafluoroborate.

3. A solution as claimed in claim 2 in which the sulfate is selected from the group consisting of 5-sulfosalicylic acid, p-toluenesulfonic acid and mixtures thereof.

4. A solution as claimed in claim 3 in which the complexing agent is ethylenediaminetetracetic acid.

5. A solution as claimed in claim 1 in which the organic sulfate is selected from the group consisting of 5-sulfosalicylic acid, p-toluenesulfonic acid and mixtures thereof.

6. A stable liquid single reagent solution for determination of direct bilirubin in sera which comprises an essentially surfactant free aqueous solution containing a positive amount up to about 10 g/l of a water soluble organic sulfate, from about 0.01 to about 0.03 g/l of a diazonium salt, from about 20 to about 30 g/l urea and a heavy metal complexing agent present in amount sufficient to complex with heavy metal ions, said solution having a pH less than 1 and stable for at least 18 months at 2 to 8° C.

7. A solution as claimed in claim 6 in which the diazonium salt is 3,5-dichlorophenyl diazonium tetrafluoroborate.

8. A solution as claimed in claim 7 in which the sulfate is selected from the group consisting of 5-sulfosalicylic acid, p-toluenesulfonic acid and mixtures thereof.

9. A solution as claimed in claim 6 in which the organic sulfate is selected from the group consisting of 5-sulfosalicylic acid, p-toluenesulfonic acid and mixtures thereof.

10. A solution as claimed in claim 6 in which the complexing agent is ethylenediaminetetracetic acid.

11. A time stable single reagent solution for the determination of direct bilirubin in sera which comprises:
   a) ethylenediaminetetracetic acid in an amount of about 0.05 g/l;
   5-sulfosalicylic acid in an amount of about 2.0 g/l;
   c) 50% $H_2SO_4$ in an amount of about 80 ml/l;
   d) conc. HCl in an amount of about 14 ml/l;
   e) urea in an amount of about 25.0 g/l and
   f) 3,5-dichlorophenyl diazonium tetrafluoroborate in an amount of about 0.02 g/l
said solution being a pH less than 1 and stable at 2-8° C. for at least 18 months.

12. A method of forming a time stable single liquid reagent for the determination of direct bilirubin in sera which comprises dissolving in water in the following sequence:
   a) a metal complexing agent in an amount sufficient to complex any heavy metal ions present,
   b) a positive amount up to about 10 g/l of a soluble organic sulfate,
   c) an acid selected from the group consisting of sulfuric acid, hydrochloric acid and mixtures thereof sufficient to reduce pH below 1, d) urea in a concentration of from about 20 to about 30 g/l and, e) 0.01 to about 0.03 g/l of a diazonium salt, to form a solution that is clear, essentially surfactant free and stable at a temperature of from about 2 to about 8° C. for at least about 18 months.

13. A method as claimed in claim 12 in which the diazonium salt is 3,5-dichlorophenyl diazonium tetrafluoroborate.

14. A method as claimed in claim 13 in which the sulfate is selected from the group consisting of 5-sulfosalicylic acid, p-toluenesulfonic acid and mixtures thereof.

15. A method as claimed in claim 12 in which the sulfate is selected from the group consisting of 5-sulfosalicylic acid, p-toluenesulfonic acid and mixtures thereof.

16. A method as claimed in claim 12 in which the complexing agent is ethylenediaminetetracetic acid.

17. A method of joining a time stable single liquid reagent for the determination of conjugated bilirubin in sera which comprises dissolving in essentially surfactant free water in the following sequence:

a) ethylenediamine tetracetic acid to a concentration of about 0.05 g/l;

b) 5-sulfosalicylic acid to a concentration of 2.0 g/l;

c) 50% $H_2SO_4$ added in an amount of about 80 ml per liter;

d) conc. HCl added in an amount of about 14 ml per liter;

e) urea to a concentration of about 25.0 g/l and, f) 3;5-dichlorophenyl diazonium tetrafluoroborate to a concentration of about 0.02 g/l, to form a solution having a pH less than 1 and stable at a temperature of from about 2 to 8° C. for at least about 18 months.

* * * * *

UNITED STATES PATENT AND TRADEMARK OFFICE
CERTIFICATE OF CORRECTION

PATENT NO. : 5,112,769

DATED : May 12, 1992

INVENTOR(S) : Ivan E. Modrovich

Page 1 of 2

It is certified that error appears in the above-identified patent and that said Letters Patent is hereby corrected as shown below:

```
Column 1, line 11, change "4,915,210" to -- 4,965,210 --.
Column 1, line 68, change "8.C" to -- 8°C --.

Column 2, line 7, after "which is" insert -- a --.
Column 2, lines 9,14, before "amount" insert -- an --.
Column 2, line 22, change "5-sulfosa:icylic" to
          -- 5-sulfosalicylic --.

Column 3, line 11, change "abut" to -- about --.
Column 3, line 17, change ",against" to -- against --.
Column 3, line 18, delete "is" (second occurrence).
Column 3, lines 41,42, after "supplied" delete
          "ready to use".
Column 3, line 45, after "reagent" change "then" to
          -- there --.
Column 3, line 59, after "absorbance" delete "is used".
Column 3, line 62, change "chemTrak TM" to -- chemTrak™ --.

Column 4, line 10, change "8°πC" to -- 8°C --.
Column 4, line 50, before "5-sulfosalicylic" insert
          -- b) --.

Column 5, line 2, change "30 g/l and," to -- 30 g/l, and --.

Column 6, line 7, change "ethylenediamine tetracetic" to
          -- ethylenediaminetetracetic --.
```

UNITED STATES PATENT AND TRADEMARK OFFICE
CERTIFICATE OF CORRECTION

PATENT NO. : 5,112,769
DATED : May 12, 1992
INVENTOR(S) : Ivan E. Modrovich

It is certified that error appears in the above-identified patent and that said Letters Patent is hereby corrected as shown below:

Column 6, line 14, change "25.0 g/l and," to
-- 25.0 g/l, and --.
Column 6, line 15, change "3;5-dichlorophenyl" to
-- 3,5-dichlorophenyl --.
Column 6, line 16, after "g/l" delete the comma.

Signed and Sealed this

Twenty-eighth Day of September, 1993

Attest:

BRUCE LEHMAN

*Attesting Officer*

*Commissioner of Patents and Trademarks*